United States Patent
Mahr et al.

(10) Patent No.: US 10,492,932 B2
(45) Date of Patent: Dec. 3, 2019

(54) DEVICE FOR SPLINTING A CAVITY, ORGAN DUCT AND/OR VESSEL

(71) Applicant: Klaus Düring, Frechen (DE)

(72) Inventors: Richard Mahr, Schrobenhausen (DE); Joachin Georg Pfeffer, Aachen (DE)

(73) Assignee: Klaus Düring, Frechen (DE)

( * ) Notice: Subject to any disclaimer, the term of this patent is extended or adjusted under 35 U.S.C. 154(b) by 0 days.

(21) Appl. No.: 13/632,596

(22) Filed: Oct. 1, 2012

(65) Prior Publication Data
US 2013/0090720 A1    Apr. 11, 2013

Related U.S. Application Data

(63) Continuation-in-part of application No. 12/096,457, filed as application No. PCT/DE2006/002137 on Dec. 1, 2006, now abandoned.

(30) Foreign Application Priority Data

Dec. 6, 2005   (DE) .................. 10 2005 058 242
Aug. 29, 2006  (DE) .................. 10 2006 040 301

(51) Int. Cl.
| A61F 2/82 | (2013.01) |
| A61F 5/56 | (2006.01) |
| A61F 2/86 | (2013.01) |
| D04C 1/06 | (2006.01) |
| A61F 2/90 | (2013.01) |

(Continued)

(52) U.S. Cl.
CPC ............. *A61F 2/82* (2013.01); *A61F 2/86* (2013.01); *A61F 2/90* (2013.01); *A61F 5/56* (2013.01); *D04C 1/06* (2013.01); *A61F 2/186* (2013.01); *A61F 2/91* (2013.01); *A61F 2/962* (2013.01);

(Continued)

(58) Field of Classification Search
CPC ........ A61F 5/56; A61F 2/06; A61F 2002/077; A61F 5/566; A61F 2/04; A61F 2002/046; A61F 2002/3698; A61F 2/848; A61F 2002/8483; A61F 2/01; A61F 2/82; A61F 2/86; A61F 2/90; A61F 2002/016; A61F 2250/0023; A61F 2250/0029; A61F 2250/0039; A61F 2230/0063; A61B 17/24; A61B 2017/248
USPC ..... 128/848, 200.24, 200.26; 623/1.13, 1.16, 623/1.3, 1.31, 1.53, 903, 1.54; 606/191, 606/194, 196

See application file for complete search history.

(56) References Cited

U.S. PATENT DOCUMENTS 5,071,407 A * 12/1991 Termin ................. A61F 2/88
                                                    604/104
5,503,636 A *  4/1996 Schmitt et al. ................ 623/1.2
(Continued)

FOREIGN PATENT DOCUMENTS

| DE | 102 40 725 | 3/2004 |
| JP | 09-173469  | 7/1997 |

(Continued)

*Primary Examiner* — Kari K Rodriquez
*Assistant Examiner* — Camtu T Nguyen
(74) *Attorney, Agent, or Firm* — Tristan A. Fuierer; Marianne Furierer; Olive Law Group, PLLC (57) ABSTRACT

The invention relates to a device for splinting and/or maintaining a cavity, an organ duct and or a vessel in a human or animal body, said device including at least one compressible and self-expanding stent that is composed of at least three phases.

11 Claims, 6 Drawing Sheets

(51) Int. Cl.
*A61F 2/91* (2013.01)
*A61F 2/962* (2013.01)
*A61F 2/18* (2006.01)

(52) U.S. Cl.
CPC ............... *A61F 2250/0039* (2013.01); *A61F 2250/0048* (2013.01); *D10B 2509/06* (2013.01)

(56) References Cited

U.S. PATENT DOCUMENTS

| | | | | |
|---|---|---|---|---|
| 5,741,333 | A * | 4/1998 | Frid .................... | A61F 2/90 623/1.18 |
| 5,800,519 | A * | 9/1998 | Sandock .................... | 623/1.22 |
| 6,475,234 | B1 * | 11/2002 | Richter et al. ............... | 623/1.15 |
| 6,551,352 | B2 * | 4/2003 | Clerc et al. .................... | 623/1.2 |
| 6,860,900 | B2 * | 3/2005 | Clerc .................... | A61F 2/856 623/1.15 |
| 8,439,963 | B2 * | 5/2013 | Dickinson et al. .......... | 623/1.13 |
| 8,568,438 | B2 * | 10/2013 | Burbank et al. ............. | 606/196 |
| 8,657,879 | B2 * | 2/2014 | Shalon et al. .................. | 623/9 |
| 8,833,373 | B2 * | 9/2014 | Barodka .................... | 128/848 |
| 2001/0044647 | A1 | 11/2001 | Pinchuk | |
| 2003/0153973 | A1 * | 8/2003 | Soun .................... | A61F 2/90 623/1.16 |
| 2004/0020492 | A1 * | 2/2004 | Dubrul .................... | A61F 5/56 128/207.18 |
| 2004/0134491 | A1 | 7/2004 | Pflueger | |
| 2004/0199243 | A1 * | 10/2004 | Yodfat .................... | A61F 2/01 623/1.16 |
| 2005/0021072 | A1 * | 1/2005 | Wallace .................... | 606/195 |
| 2005/0245906 | A1 * | 11/2005 | Makower .................... | A61B 5/06 604/891.1 |
| 2005/0288775 | A1 * | 12/2005 | Dong .................... | A61F 2/07 623/1.54 |
| 2006/0048775 | A1 * | 3/2006 | Dunlap .................... | 128/200.26 |
| 2006/0149350 | A1 * | 7/2006 | Patel .................... | A61F 2/954 623/1.11 |
| 2006/0155358 | A1 * | 7/2006 | LaDuca .................... | A61F 2/844 623/1.11 |
| 2008/0053458 | A1 * | 3/2008 | De Silva et al. ......... | 128/207.18 |
| 2008/0262597 | A1 * | 10/2008 | Xiao .................... | A61B 17/064 623/1.15 |
| 2009/0266365 | A1 * | 10/2009 | Oberle .................... | 128/207.18 |
| 2011/0054589 | A1 * | 3/2011 | Bashiri .................... | A61F 2/90 623/1.15 |

FOREIGN PATENT DOCUMENTS

| | | |
|---|---|---|
| JP | 2003-019209 | 1/2003 |
| JP | 2003-265621 | 9/2003 |
| JP | 2004-167239 | 6/2004 |
| WO | WO 96/31249 | * 10/1996 |
| WO | WO 98/23233 | 6/1998 |

* cited by examiner

○ = Return -Point

Fig. 6

○ = Return -Point

Fig. 7

○ = Return -Point

Fig. 8

DEVICE FOR SPLINTING A CAVITY, ORGAN DUCT AND/OR VESSEL

CROSS REFERENCE TO RELATED APPLICATIONS

This is a Continuation-in-Part Application claiming priority to co-pending U.S. patent application Ser. No. 12/096,457 filed on Aug. 12, 2010, which in turn was filed under the provisions of 35 U.S.C. § 371 and claims the priority of International Patent Application No. PCT/DE2006/002137 filed on Dec. 1, 2006, which in turn claims priority of German Patent Application No. 10 2005 058 242.7 filed on Dec. 6, 2005 and German Patent Application No. 10 2006 040 301.0 filed on Aug. 29, 2006.

BACKGROUND OF THE INVENTION

Technical Field

The present invention relates to a device for the splinting and/or holding open of a cavity, an organ duct and/or a vessel in the human or animal body with at least one compressible and self-expanding stent which has at least one expanded phase.

Prior Art

Syndromes based on the at least partial closure of cavities, organ ducts and/or vessels are increasing sharply due to the effects of civilisation. An important area of such syndromes relates to the air passages. For example obstructive sleep apnea is a life-threatening illness resulting from the closure of the rear air passages due to muscle relaxation during sleep. Through repeated and sometimes very frequent interruption of breathing during sleep, the patient is not adequately supplied with oxygen, in extreme cases leading to death. Civilisation-related factors such as e.g. severe obesity or excessive alcohol consumption seriously increase the risk of illness. Snoring is a gentler outcome of the effect than sleep apnea, but results from the same organic cause. Whereas people are aware of snoring, the serious risks to health especially of heavy snoring and of sleep apnea are often not registered, since the patient is not aware of the organic deficiency symptoms.

Figure 1:
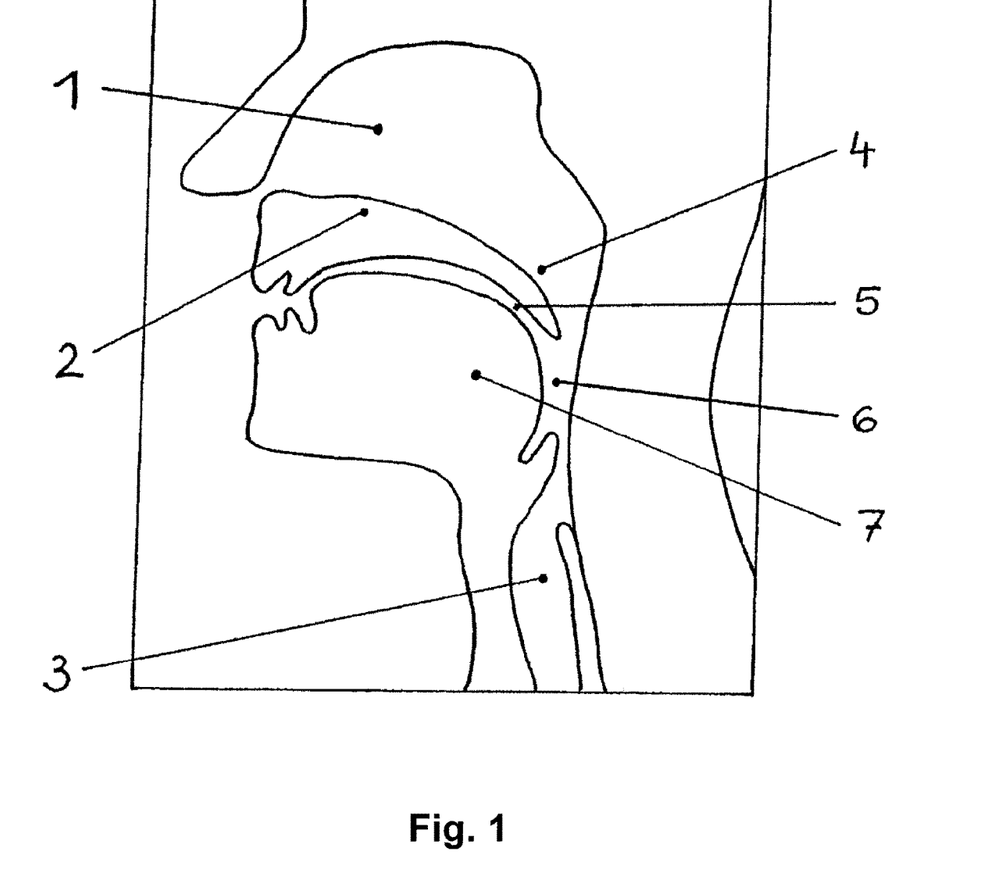
FIG. 1 the free air passage during sleep.
Figure 2:
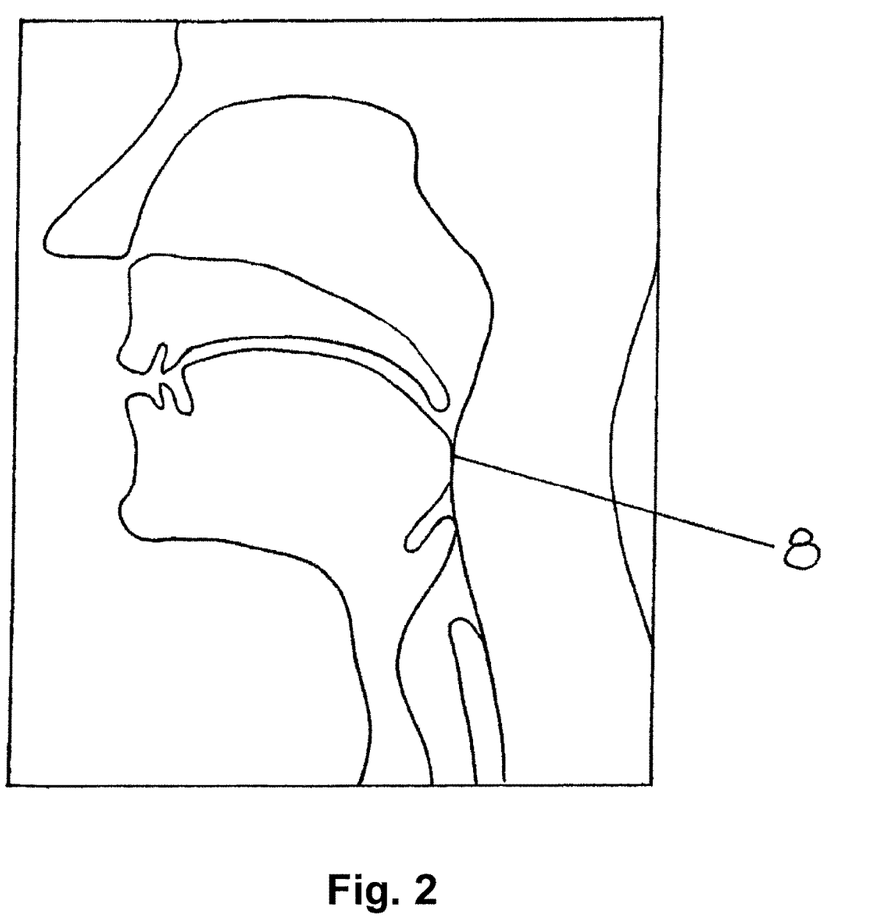
FIG. 2 the blocked air passage during sleep as the cause of snoring and obstructive sleep apnea, and FIG. 3 the opening of the air passages by n-CPAP therapy.

FIG. 1 shows free airways through which normal breathing takes place. The relaxation of the tongue and of the surrounding muscles in the pharyngeal cavity which occurs during sleep leads, due to the inflowing air, to vibrations of the soft palate and the soft parts of the throat, resulting in the noise of snoring. Strong relaxation of the throat tissue and the falling back of the root of the tongue may lead to complete closure of the air passages (FIG. 2). After a certain time (approx. 60-90 seconds) the brain generates a waking reaction. The transition from snoring to apnea is fleeting. The interruption of breathing may last up to 1.5 minutes and be repeated 200-400 times during the night, which does not allow the patient any deep sleep. The consequences are restless sleep, tiredness during the day, high blood pressure, lack of drive, etc. If the illness is not treated, then the body is unable to regenerate adequately in sleep, leading to a lower expectation of life. Increased fluctuations of pressure within the thorax may in certain circumstances have adverse effects on the cardiovascular system. Consequences of snoring are high blood pressure and a drop in the oxygen content of the blood. It is nowadays assumed that in particular during sleep apnea, but also during snoring, significant organic consequent illnesses may occur.

The Health Technology Assessment Report, volume 25 "The Sleep Apnea Syndrome" by Perleth et al., Asgard Verlag St. Augustin 2003, establishes on the basis of epidemiological studies a prevalence of sleep apnea among around 2-4% of the population of Germany, i.e. roughly 2 to 3 million affected persons. In diagnostic tests conducted in sleep laboratories, accordingly, around half of all patients turned out to be affected by apnea and urgently in need of treatment. Other sources assume a proportion of only 5% for diagnosed illness treated by therapy. According to Prof. Dr. Frank Michael Baer of the University Clinic, Cologne, a third of the male population of Germany are regular snorers. Snoring requires treatment for 4% of men and 2% of women aged between 30 and 60 years. At the same time, the incidence of snoring rises sharply with age. Thus, while only about 10% of the population snore at the age of 20, this rises to around 50% at the age of 50. In short, sleep apnea is an illness of socially relevant character with increasing prevalence and importance, in which only a small portion of those affected are known and receiving treatment. There is therefore also a need for new, simple, but effective options for therapy.

Figure 3:
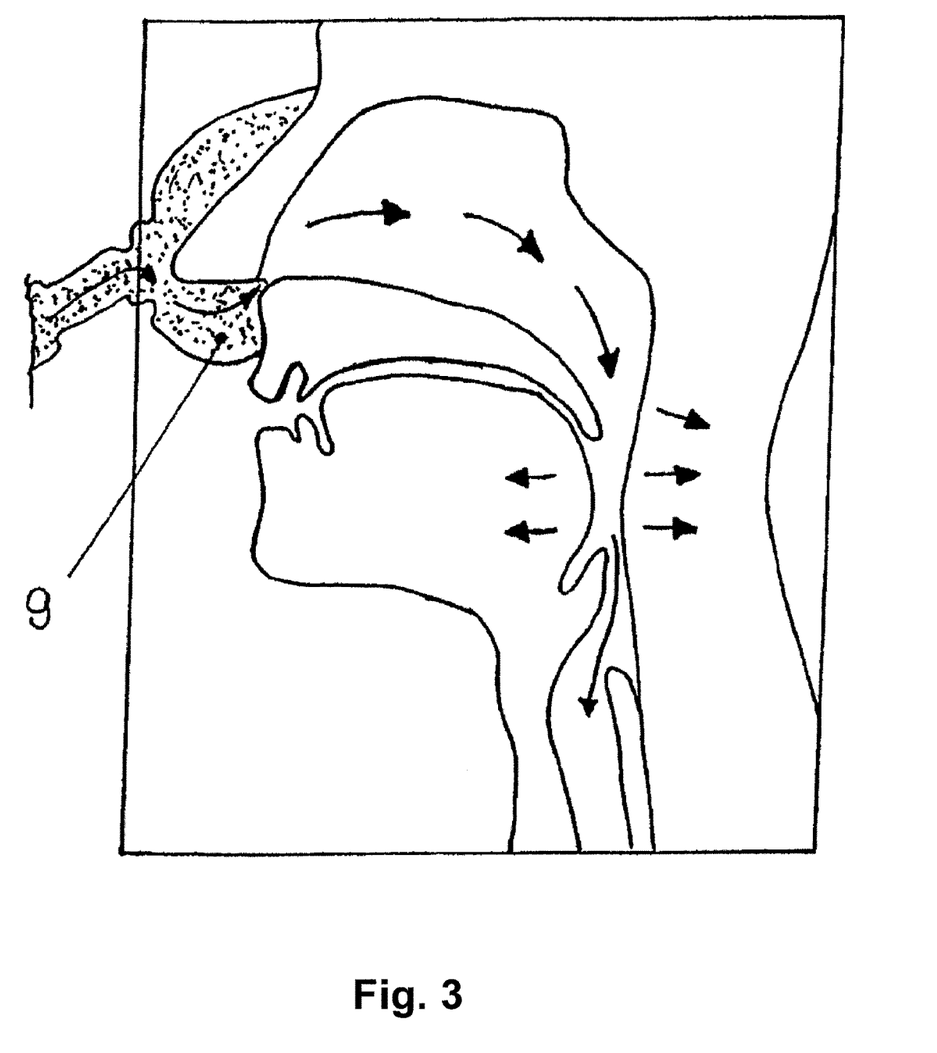

The current standard therapy for sleep apnea is the active supply to the patient of respiratory air under overpressure by means of an n-CPAP breathing apparatus (nasal continuous positive airway pressure). Through the night-time wearing of a breathing mask, through which a continuous positive airway pressure is generated, the air passages are held sufficiently open. The principle of operation is illustrated in FIG. 3. Significant drawbacks to this standard therapy, which is to date the sole treatment option with medical effectiveness, are the discomforts to the patient, created above all by the wearing of an airtight oxygen mask for the whole night, fixed via an adequately strong headband and connected via the supply tube to the breathing apparatus; also through drying out of the mucous membranes and the need for moistening of the respiratory air, plus the operating noise of the breathing apparatus. In addition to the severely restricted freedom of movement during sleep, there is the risk of air escaping due to leaks between the breathing mask and the skin of the face, so that the overpressure is accidentally reduced and may no longer be sufficient. Moreover, acceptance of the nightly wearing of a breathing mask is very limited in time for many patients, even though life-long therapy is required. The HTA report referred to above reported that the acceptance of CPAP treatment, in particular long-term, is relatively low. Less than half of patients to whom CPAP was recommended carried out the treatment long-term (i.e. for more than one month). It was notable that, despite proof of significant therapeutic effectiveness only for the CPAP mask, there was a clear but subjective preference by patients for an intraoral splint, probably due to the lower subjective stress of this therapy. The intraoral splint is claimed to provide at least partial improvement of symptoms by ensuring breathing through the mouth. A further drawback of the CPAP mask is the need to take the breathing apparatus with one when travelling. There is also the time and effort required for cleaning and maintenance.

On account of these severe stresses and restrictions for the patient, apnea patients suffer a high degree of mental trauma and have great interest in alternative and subjectively more tolerable therapy options. The prevailing view is that as yet no efficient alternative treatment option has been developed which may be used routinely, and is also practicable and cost-effective.

A large number of proposals have been made for the physical prevention of snoring and apnea, but none have become established on the market. Described in DE 195 01 363 is a device for insertion through the mouth, characterised by a tube which may be introduced into and fixed in the pharynx. It is meant to prevent the collapse of the soft parts of the pharynx. A drawback cited by the inventor is the need to overcome nausea. Experience shows that the route described here, via the mouth, is impracticable, and does not lead to adequate reduction of symptoms. A similar device to support the soft palate parts in the nose and throat area, but which is intended for introduction through the nose, is proposed in DE 100 28 013. The effect is just as limited as the instrument described above. Alternatively, in WO 98/23233 it is proposed to introduce a double tube through the nose to maintain the air supply passage, but this is just as ineffective as the two instruments described above. DE 102 40 725 describes a probe against apnea and snoring, which is expandable at the end by means of a drawing element. It is not described how in practice the expansion by means of the drawing element takes place or how the expanded probe is stabilised in the air passage.

SUMMARY OF THE INVENTION

The present invention is now based on the problem on the one hand of avoiding the aforementioned drawbacks of the prior art, and on the other hand of making possible a practicable splinting and/or holding open of cavities, organ ducts and/or vessels in the human or animal body. Here, for the treatment of illnesses such as snoring and apnea, repeated daily use of a device according to the invention is necessary, and therefore special requirements are placed on the durability of any such medical instrument. At the same time the principle according to the invention for the device should be effective not only specifically in the air passages for the treatment of snoring and/or sleep apnea, but should also be capable of application for the splinting and/or holding open of other cavities, organ ducts and/or vessels in the human or animal body.

The problem is solved by a device for the splinting and/or holding open of cavities, organ ducts and/or vessels in the human or animal body with at least one self-expanding stent which is compressible in a tube and develops at least two phases, characterised in that at least one phase of the stent has a greater expansion, i.e. a greater diameter in the expanded state. In a preferred embodiment, the distal end of the at least one stent is expanded. The problem is further solved by providing that the at least one stent in a further preferred embodiment may be made to have at least three phases, and the different phases of the at least one stent may have different degrees of expansion, wherein the at least one transition phase so connects the at least two functional phases with one another that the latter may assume their configuration unaffected by one another. In an even more preferred embodiment, the at least one transition phase is formed by the twining around of at least two wires, fibres and/or threads ("twist"). Developments of the invention are defined in the relevant dependent claims.

In this way a device is created which, in the compressed state, is inserted in the cavity, organ duct and/or vessel after which, by drawing back an outer tube, the inner at least one stent is released, self-expands and, at least with the phase of greatest expansion, fits up against the wall of the cavity, organ duct and/or vessel. By pushing the tube back over the expanded stent, the device may be compressed again and easily removed from the cavity, organ duct and/or vessel. By means of the expanded stent, the cavity, organ duct and/or vessel is splinted and/or held open. The tube containing the compressed stent is so dimensioned that it may easily be inserted into the cavity, organ duct and/or vessel, even when the cavity, organ duct and/or vessel is in a collapsed state. Preferably the stent is made of a shape memory material. In the operating state, the device is expanded only over a small part in one phase of the stent, again preferably at the distal end, while the other part at the other end of the stent undergoes only a fairly limited expansion on release from the tube. The size and length relationships of the phases of the at least one stent relative to one another may be freely selected.

Due to the elastic construction of the stent and the elasticity of the surrounding tube, the device may easily follow any curvature of the cavity, organ duct and/or vessel. Optimal adaptation of the stent to the anatomy of the cavity, organ duct and/or vessel is possible with very great ease, due to the scope for varying the elastic expansion of the stent.

Preferably the stent has a net structure and/or a multiplicity of openings with different angles of opening and/or opening widths in the phases. It is especially preferred for the stent to be made of braiding and/or woven fabric and/or interlaid scrim, in particular from a wire, thread and/or fibre braiding or woven fabric or interlaid scrim. In another embodiment, the at least one stent may be made from a tube slit over at least part of its length, and produced in an especially preferred manner e.g. by laser cutting of a metal or nitinol tube.

Through the expanded phase with the greater diameter of the at least one stent, a reliable and defined expansion for the splinting and/or holding open of the cavity, organ duct and/or vessel only in a specific, pre-defined area of the stent is ensured. In the at least one proximal phase, the stent has preferably smaller angles of opening in its longitudinal direction, and in the at least one distal phase the stent has preferably larger angles of opening in its longitudinal direction, so that the necessary force for expansion, splinting and/or holding open of the cavity, organ duct and/or vessel in this area can be obtained. In another preferred embodiment, the angles of opening in the longitudinal direction of the stent may be larger in the at least one proximal phase and smaller in the at least one distal phase. In a preferred embodiment with at least three phases, in order to create a transition zone between two functional phases of the stent in the at least one transition phase, the stent is comprised preferably of openings which are larger than those in the functional phases, so that after release from the tube they may adopt their configuration uninfluenced by one another. In an especially preferred version this is obtained by a twisting of at least two wires, fibres and/or threads. In another preferred embodiment these openings may be made by laser cutting in a metal or nitinol tube.

The material of the at least one stent may be provided with a coating, in particular with a bio-compatible surface coating, heparin, a carbonisation of nitinol, a nano-technological coating, x-ray-proof particles, a coating releasing an active substance, a preferably microporous bio-technological, or another other coating. Through the provision of such a coating, in addition to the physical effect, a pharmaceutical effect for example may also be provided. Moreover, by providing a coating which roughens the surface of the stent, fixing of the stent at the point of action is improved. In this connection, though, care is preferably taken to avoid any damage to the respective wall of the cavity, organ duct and/or vessel in the human or animal body in which the stent is used.

Preferably the at least one stent is/are made of a biocompatible shape memory material, in particular a metal or a metal alloy, in particular a stainless steel or nitinol or another bio-compatible material, such as in particular a plastic, or monofile and/or multifile and/or composite glass fibres. Since the stent remains for at least several hours up to days in the human body, it is especially advantageous to use a bio-compatible material to avoid rejection effects and allergic reactions. To impress upon the stent the expanded form, with subsequent compression, and to allow it to open through self-expansion, a shape memory material is advantageously chosen.

In an even more preferred embodiment, the stent has at the distal end round ends, i.e. the wire or fibre or thread is guided back into the braiding or woven fabric or interlaid scrim, so that there are no open wire or fibre or thread ends at the distal end of the stent, which could lead to damage to the relevant wall of the cavity, organ duct and/or vessel. In an even more preferred embodiment, the round ends at the distal end are bent slightly inwards.

In a preferred embodiment the proximal end of the stent is fixed by at least one end of the wire or fibre or thread, which is open by virtue of its construction, in a closure, e.g. bonded. In the same way, connection may also be made to a pulling element, with the aid of which the stent together with the tube may be inserted in and removed from the cavity, organ duct and/or vessel. In an even more preferred embodiment, this closure is a threaded closure.

To protect the stent from slipping into the cavity, organ duct and/or vessel, the stent may be provided at the proximal end with a fastening, which in a preferred embodiment may be adjusted variably to the anatomical features concerned in each case. The tube may be longer, the same length or shorter than the stent, and where necessary extended by an additional piece needed for handling, downwards from the stent, e.g. beyond the pulling element, and with which it may be adapted flexibly to the particular conditions of use. In a preferred manner of use, the device may be pushed forward directly up to the point of use and there released by withdrawing the tube from the stent. This may involve partial or complete withdrawal of the tube. In another preferred embodiment, the device may be pushed forward until just before the point of use only, and then the stent pushed out of the tube forward to the point of use, after which the tube is withdrawn wholly or partly or is even not withdrawn at all.

For the treatment of snoring and/or apnea the device is preferably so dimensioned that the distal end of the at least one stent just reaches the epiglottis, to avoid irritation of the pharynx and nausea. Here the distal expanded phase of the stent preferably has a length of 0.5 cm to 20 cm. The whole stent preferably has a length of 2 cm to 50 cm. The length of the tube is preferably between 0.5 cm and 50 cm. In a most preferred embodiment, the whole stent has a length of 10 cm to 35 cm with a distal expanded phase between 1 cm and 10 cm in length, and with a 10 cm to 35 cm long tube. It has been shown that, with such a device in the dimensions described and for human use, the air passages may be reliably and reproducibly held open during sleep, and the oxygen saturation in the blood for an apnea patient is able to rise above the critical limit value of 90%. Consequently, replacement of the n-CPAP breathing mask by the device according to the invention for the splinting and/or holding open of a cavity, organ duct and/or vessel is possible easily, efficiently and with very good physical tolerance by the patient.

In a similar manner to the treatment of snoring and/or sleep apnea, it is possible to use the device according to the invention for the treatment of bronchial stenosis, bile duct constrictions and for the splinting and/or holding open of blood vessels, lymph vessels, urinary ducts, Fallopian tubes and sections of bowel. This list is not intended to be limiting for the range of application of a device according to the invention, but is rather meant to illustrate the breadth of scope for such application.

BRIEF DESCRIPTION OF THE INVENTION

For a more detailed explanation of the invention, embodiments will be described in detail below with the aid of the drawings, which show in.

DETAILED DESCRIPTION OF THE INVENTION

FIG. 1 shows the nasal chamber (1), the hard palate (2), the trachea (3), the soft palate (4), the oral cavity (5), the free airways (6) and the tongue (7). Illustrated is the free airway during sleep of a healthy person. FIG. 2 shows the closed airway (8) in the pharynx, as occurs in obstructive sleep apnea. FIG. 3 shows the use of the n-CPAP breathing apparatus with the breathing mask (9) in place, and the air passages opened by the overpressure.

Figure 4:
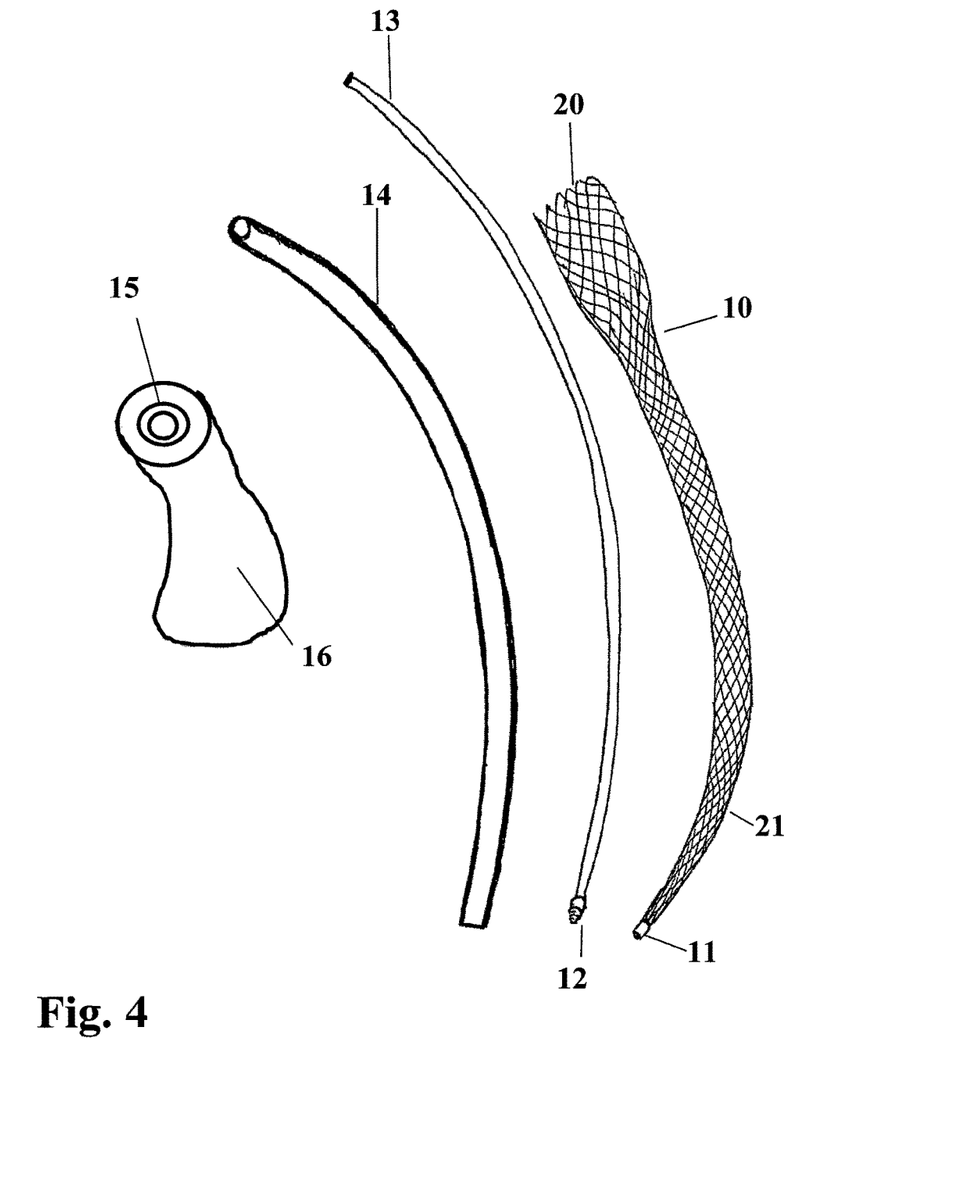
FIG. 4 shows a view of the components of a first embodiment of a device according to the invention for the splinting and/or holding open of a cavity, organ duct and/or vessel with a three-phase stent.

FIG. 4 shows a view of the components of a first embodiment of a device according to the invention for the splinting and/or holding open of a cavity, organ duct and/or vessel in a human or animal body. The device comprises a three-phase stent (10), connected at its proximal end (21) via a connecting element (11) to the connecting element (12) of a pulling element (13). To insert the stent into the cavity, organ duct and/or vessel, the stent is inserted into the tube (14) and compressed. At its proximal end (21), the stent (10) is firmly fixed in a connecting element (11). By this means, in the possible presence for design reasons of an open wire or fibre or thread end at the proximal end (21) of the stent (10), its cohesion is simultaneously ensured. Also created via the connecting element (11), which may contain e.g. a screw thread, is the connection to the connecting element (12) of the pulling element (13), which may similarly contain a screw thread. The tube (14) may be made preferably of a plastic polymer, for example a PTFE, PVC, PE, PU, silicon or Teflon tube, or be a catheter. The pulling element (13) may be made preferably of a plastic, a metal or a metal alloy, or glass fibre materials. In another embodiment, the two connecting elements (11) and (12) may be produced as a single solid element, so that the stent (10) is permanently connected to the pulling element (13).

For the use of a device according to the invention for the treatment of snoring and/or sleep apnea, the device is inserted, compressed in the tube (14), into one of the two nostrils and preferably pushed forward as far as possible towards the epiglottis, and positioned at its point of use. By withdrawing the tube (14), the stent (10) is released, and self-expands to its pre-impressed size. This prevents the collapse of the pharynx and the closing of the air passages. A free airflow and normal breathing are thereby made possible. In a further embodiment, to set the depth of insertion and to prevent the stent from accidentally slipping into the air passage, a fastening (15) may be fixed at the proximal end (21) of the stent (10). A mounting plate (16) may also be provided to prevent the stent from accidentally slipping into the air passage and the pharynx. After insertion of the device and release of the stent (10) by withdrawing the tube (14), the pulling element (13) is separated and removed from the stent (10) by releasing the connecting element (12) from the connecting element (11). In this phase and fixed by the fastening (15) and if applicable the mounting plate (16), the stent is worn during sleep. In a further embodiment, an additional fastening of the stent to the head may be provided as security against it slipping out of the air passage. This may be provided for example by a soft headband, which may be fastened to the mounting plate.

Figure 5:
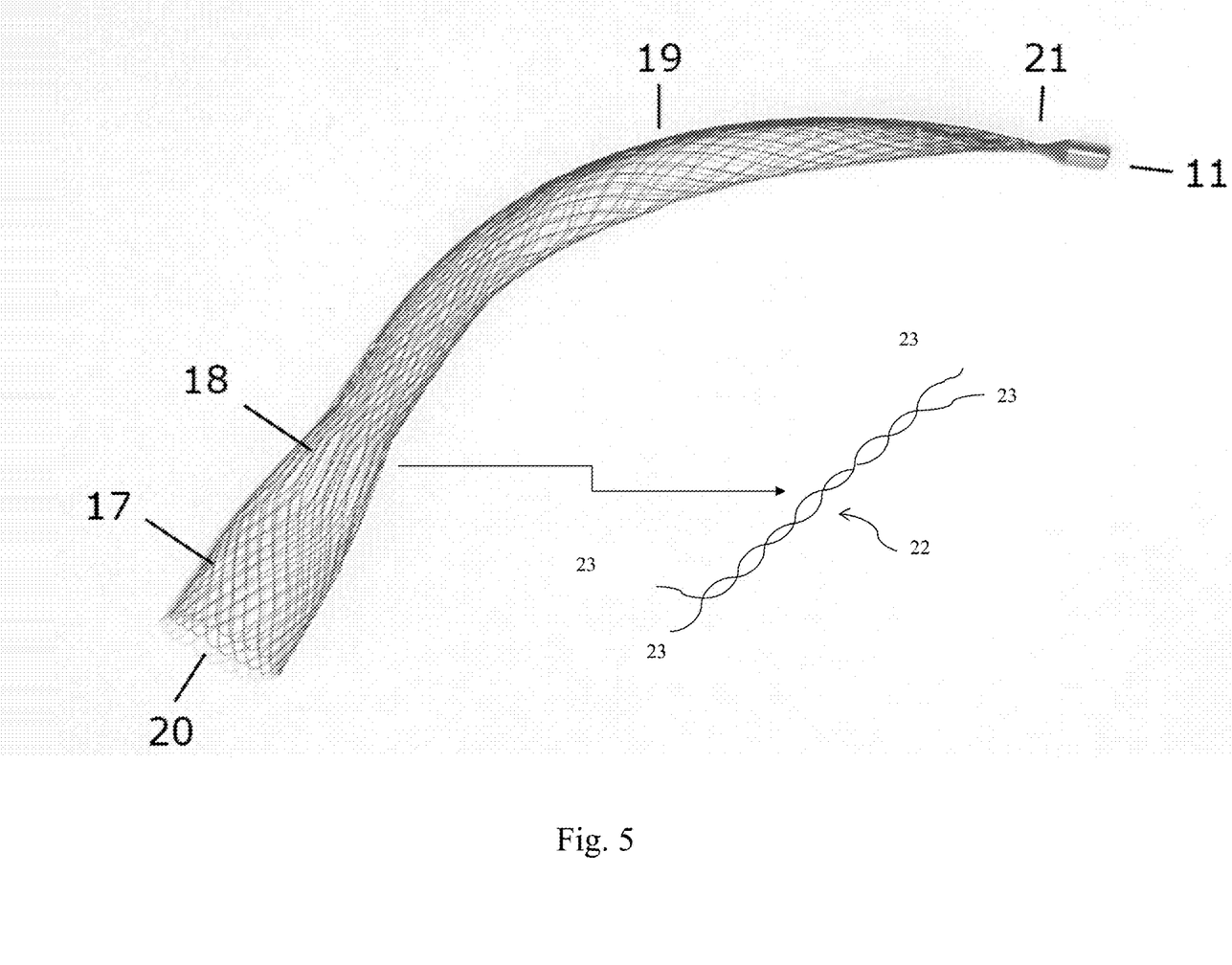
FIG. 5 shows a view of a three-phase stent of a first embodiment of a device according to the invention.

FIG. 5 shows a view of a three-phase stent (10) in a first embodiment of a device according to the invention for the splinting and/or holding open of a cavity, organ duct and/or vessel in a human or animal body for the treatment of snoring and/or sleep apnea. The distal functional phase (17) of the stent is in this first embodiment the therapeutically active part of the medical device, which is expanded sufficiently to hold open the air passages. The proximal functional phase (19) of the stent may be used in particular for locating the stent in the nasal area and is accordingly expanded only slightly. The distal phase (17) therefore has a greater expansion diameter than the proximal phase (19). To ensure reliably the differing expansion of the distal phase (17) and the proximal phase (19) of the stent (10), and also to achieve this for many times repeated use of the device, involving on each occasion an opening and a closing process, the distal phase (17) and the proximal phase (19) are connected to one another by a transition phase (18), preferably twisted together and which, through the stability of the twisted wires, fibre or threads allows the distal phases to assume their configuration, uninfluenced by one another, after release from the tube. The design of the stent (10), in this form of at least three phases, composed of at least two functional phases and at least one transition phase is an important element of an embodiment of a device according to the invention and thus distinguishes the stent (10) significantly from the nowadays generally common stents for the canalisation or holding open of e.g. blood vessels.

In principle, the phase with the greatest diameter in the expanded state of the at least three phases of the at least one stent (10) may be chosen freely. Here a transition phase (18) may have either the same or a greater or even a smaller diameter than the functional phases. The transition phase (18) is preferably created by the twisting of at least two sections of wires or of fibres or of threads (23) to form a twisting (22), while the other phases are preferably constructed through the crossing of at least a section of the wire or fibre or thread. For the construction of the less expanded phase, preferably a braiding and/or woven fabric and/or interlaid scrim with smaller angles of opening in the longitudinal direction of the stent is chosen. For the construction of the more expanded phase, preferably a braiding and/or woven fabric and/or interlaid scrim with larger angles of opening in the longitudinal direction of the stent is chosen. Importantly, this stent can be made of a single wire and thus different sections of the wire can be twisted in different formations to provide the different phases.

To obtain especially good stability of the stent combined simultaneously with optimal air permeability, the stent has a net structure. This may be formed e.g. by a wire, thread and/or fibre braiding and/or woven fabric and/or interlaid scrim. Alternatively a cut tube may be provided with such a structure, with openings of different sizes, especially preferably prepared by laser cutting of a metal or nitinol tube. The important factor here is a number of openings sufficient to allow an unimpeded air flow. The stent may therefore have a very fine network or a coarser network. In a preferred embodiment, the stent is made from a shape memory material. This may be for example nitinol, stainless steel, plastic or monofile, multifile and/or composite glass fibre material. In a preferred embodiment, the stent is made by manual or machine braiding in predefined patterns to produce the different phases.

A particular problem with repeated insertion and removal of a device according to the invention on the one hand, and possible use in open cavities on the other hand lies in the fact that open ends of a material from which the braiding and/or woven fabric and/or interlaid scrim of the stent (10) is made may lead to irritation of the wall of the cavity, organ duct and/or vessel. To avoid this problem, it is preferable for the stent (10) to have closed ends, at least at the distal end (20) of the stent. Closed ends, especially in braided systems, are at present not generally to be found in commercially available stents. Instead, these are usually open at both ends. For the device according to the invention, therefore, special new braiding patterns have been developed and stents according to the invention produced. Here the stent (10) may be made preferably of only one wire or one fibre or one thread, to give only closed ends at the distal end (20) of the stent (10), and two open wire or fibre or thread ends at the proximal end (21) of the stent (10). In another preferred embodiment, the number of wires or fibres or threads used to produce the stent (10) matches the number of closed ends required. This may be for example 12, 18 or 24 wires or fibres or threads for 12, 18 or 24 closed ends at the distal end (20) of the stent (10). This results in 24, 36 or 48 open wire or fibre or thread ends at the proximal end (21) of the stent (10). Since the proximal end (21) of the stent (10) is fixed firmly in the connecting element (11), all open ends of the wires or fibres or threads at the proximal end (21) of the stent (10) are in any case firmly tied in and represent no danger to the patient.

In choosing the strength of the wire or fibre or thread, the material properties should be balanced with the mechanical properties of the braiding and/or woven fabric and/or interlaid scrim. In a preferred embodiment, the stent (10) is made of nitinol wire with a diameter of 0.001 mm to 2 mm, even more preferably with a diameter of 0.05 mm to 0.5 mm, and most preferably with a diameter of 0.1 mm to 0.2 mm. The diameter of the nitinol wire, and the density and angle of opening of the braiding determine the forces involved in the expansion and holding open of the cavity, organ duct and/or vessel in the more strongly expanded phase of the stent (10). In certain forms of treatment such as that for snoring and sleep apnea, these forces contribute significantly to the well-being of the patient.

Figure 6:
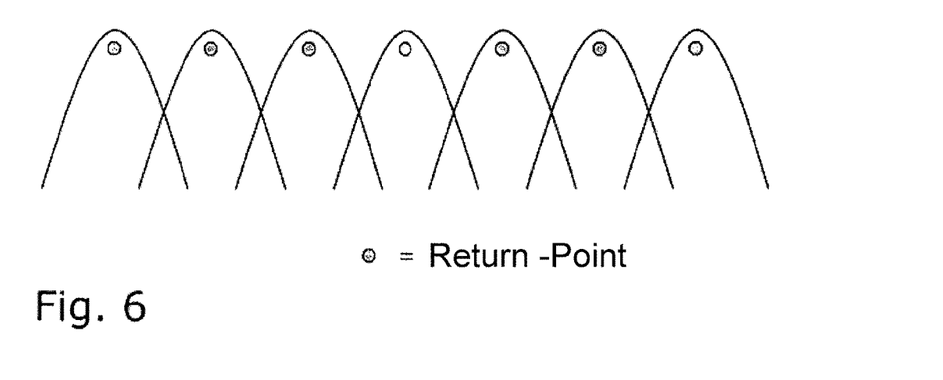
FIG. 6 shows a braiding pattern with round ends at the distal end of the braiding and/or woven fabric and/or interlaid scrim of a stent of a second embodiment of a device according to the invention, in which only one wire or fibre or thread is always guided back separately and directly.
Figure 7:
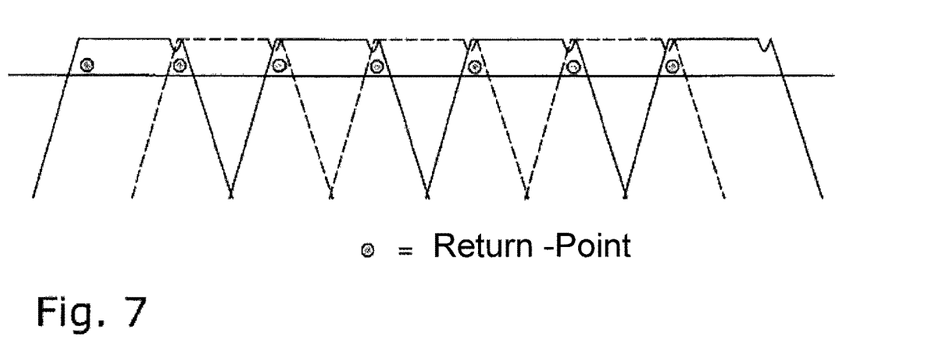
FIG. 7 shows a braiding pattern with round ends at the distal end of the braiding and/or woven fabric and/or interlaid scrim of a stent of a third embodiment of a device according to the invention, in which two wires or fibres or threads always cross at the return point.

FIG. 6 shows a braiding pattern with round ends at the distal end (20) of the stent (10) in a preferred embodiment of a device according to the invention, in which in each case only one wire or fibre or thread is guided back separately into the braiding. In a preferred embodiment, the incoming wire or fibre or thread is guided back round directly into the braiding. In another preferred embodiment (FIG. 7), the incoming wire or fibre or thread is so guided back that two wires or fibres or threads always cross at the return point. These embodiments are not intended to be limiting for possible braiding patterns for the return of one incoming wire or fibre or thread. Instead, many other suitable embodiments are possible amongst those described above and shown in FIGS. 6 and 7, in order to obtain round ends at the distal end (20) of the stent (10) in a braiding, with in each case only one single wire or fibre or thread being guided back. These other suitable embodiments are included here.

Figure 8:
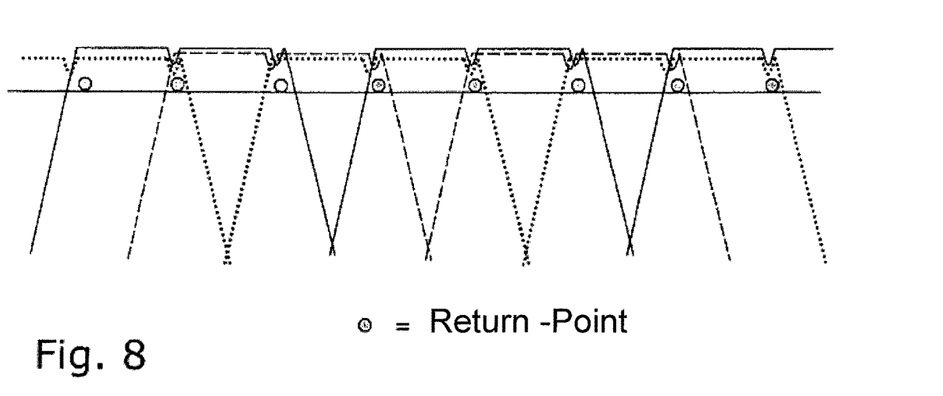
FIG. 8 shows a braiding pattern with round ends at the distal end of the braiding and/or woven fabric and/or interlaid scrim of a stent of a third embodiment of a device according to the invention, in which at least two wires or fibres or threads are guided back at least partly parallel.

FIG. 8 shows a braiding pattern with round ends at the distal end (20) of the stent (10) in a preferred embodiment of a device according to the invention, in which at least two wires or fibres or threads are guided back at least partly parallel. In a preferred embodiment, the incoming wire or fibre or thread is guided back round into the second position within the braiding pattern. In another preferred embodiment, the incoming wire or fibre or thread is guided back round into the third or subsequent position within the braiding pattern. These embodiments are not intended to be limiting for possible braiding patterns for the return of an incoming wire or fibre or thread. Instead, many other suitable embodiments are possible amongst those described above and shown in FIG. 8, in order to obtain round ends at the distal end (20) of the stent (10) in a braiding, wherein at least two wires or fibres or threads are guided back at least partly parallel. These other suitable embodiments are included here. The advantage of the braiding pattern depicted in FIGS. 7 and 8 and of similar braiding patterns is that, on the one hand, the distal end (20) of the stent (10) is given greater stability, and on the other hand greater rounding may be obtained than in the braiding patterns depicted in FIG. 6 and similar braiding patterns. This latter feature contributes to comfort in use for the patient.

In connection with the embodiments described above and shown in the figures of a device for the splinting and/or holding open of a cavity, organ duct and/or vessel in the human or animal body, it is possible for numerous further embodiments to be created. In particular the shape of the stent may be matched to the shape of the cavity or organ duct or vessel. In some cases shorter stents with a larger opening diameter are more suitable, while at other points of use narrower, longer stents may be advantageous. In the case of the embodiments described above and shown in the figures of a stent with at least three phases, numerous further embodiments may similarly be created. In each of these embodiments, at least one functional phase of the stent is connected to at least one other functional phase by a transition phase which facilitates the free development of the two different configurations of the functional phases.

LIST OF REFERENCE NUMBERS

1 nasal chamber
2 hard palate
3 trachea
4 soft palate
5 oral cavity
6 free airways
7 tongue
8 closed airways
9 nose mask of the n-CPAP apparatus
10 stent
11 connecting element
12 connecting element
13 pulling element
14 tube
15 fastening
16 mounting plate
17 distal functional phase of the stent
18 transition phase of the stent
19 proximal functional phase of the stent
20 distal end of the stent
21 proximal end of the stent That which is claimed is:

1. A stent for splinting and/or holding open of a pharynx in a human or animal body, wherein the stent comprises a distal end and a proximal end, is compressible in a tube, and is self-expanding, said stent further comprising a proximal functional phase, a distal functional phase, and a transition phase, wherein the transition phase is positioned between the two functional phases and wherein the stent has a net structure made of material comprising wire, fibre or thread, wherein a multiplicity of openings of the net structure of the transition phase are larger than the multiplicity of openings of the net structure of the two functional phases, wherein the functional phases and the transition phase are made of continuous wires, fibres, or threads extending from the proximal end to the distal end and back to the proximal end, that result in a closed, rounded end for each wire, fibre, or thread at the distal end of the stent and two open wire, fibre, or thread ends at the proximal end of the stent, wherein the number of wires, fibres or threads used to produce the stent matches the number of closed ends, and the transition phase consists of a twisting of at least two sections of the continuous wires, fibres or threads extending the length of the transition phase, wherein the distal functional phase of the stent has a greater expansion diameter than the proximal functional phase, wherein the pharynx is splinted and/or held open by at least the distal functional phase of the stent, and wherein the two open wires, fibres or threads at the proximal end are firmly fixed to a connecting element.

2. The device according to claim 1, wherein the functional phases are constructed through the crossing of at least a section of the wire, fibre or thread.

3. The device according to claim 2, wherein functional phases comprise a braiding and/or woven fabric and/or interlaid scrim with angles of opening in a longitudinal direction of the stent.

4. The device according to claim 1, wherein the distal functional phase of the stent has a length of 0.5 cm to 20 cm, the tube has a length of 0.5 cm to 50 cm and the stent has a length of 2 cm to 50 cm.

5. The device according to claim 1, wherein a total of 12, 18 or 24 wires, fibres or threads are used resulting in 12, 18 or 24 closed ends at the distal end, respectively.

6. The device according to claim 5, wherein the 12, 18 or 24 wires, fibres or threads results in 24, 36 or 48 open wires, fibres or thread ends at the proximal end, respectively.

7. The device according to claim 1, wherein the connecting element further comprises a screw thread.

8. The device according to claim 1, further comprising a pulling element removably connected to the stent at the connecting element.

9. The device according to claim 1, wherein the wires, fibres or threads of the stent has a diameter of preferably 0.001 mm to 2 mm.

10. The device according to claim 1, wherein the wires, fibres or threads of the stent has a diameter of preferably 0.05 mm to 0.5 mm.

11. A treatment method for snoring and/or sleep apnea in a subject, the method comprising inserting the stent according to claim 1 through a subject's nose into the pharynx to open the pharynx, wherein the stent is inserted into the tube and inserting the tube in the nose of the subject up the pharynx, the tube is withdrawn from the nose to release the stent from the tube, the stent expands, wherein the pharynx is splinted and/or held open by at least the distal functional phase of the stent.

* * * * *